United States Patent [19]

Okuno et al.

[11] 3,966,963
[45] June 29, 1976

[54] INSECTICIDAL COMPOSITION CONTAINING CYCLOPROPANE-CARBOXYLATE

[75] Inventors: Yoshitoshi Okuno, Toyonaka; Nobushige Itaya, Ikeda; Toshio Mizutani, Toyonaka, all of Japan

[73] Assignee: Sumitomo Chemical Company, Limited, Osaka, Japan

[22] Filed: Jan. 13, 1975

[21] Appl. No.: 540,547

Related U.S. Application Data

[62] Division of Ser. No. 364,271, May 29, 1973, Pat. No. 3,876,681.

[30] Foreign Application Priority Data

May 31, 1972 Japan.................... 47-54533

[52] U.S. Cl.................... 424/305; 424/17; 424/23; 424/40; 424/45; 424/46; 424/357
[51] Int. Cl.²................... A01N 9/24
[58] Field of Search.................. 424/305, 45, 40

[56] References Cited
UNITED STATES PATENTS 3,720,703    3/1973    Elliot et al. .................... 424/305
3,795,696    3/1974    Katsuda et al. .................... 424/305

Primary Examiner—Dale R. Ore
Attorney, Agent, or Firm—Stevens, Davis, Miller & Mosher

[57] ABSTRACT

An insecticidal composition and method containing a compound of the formula,

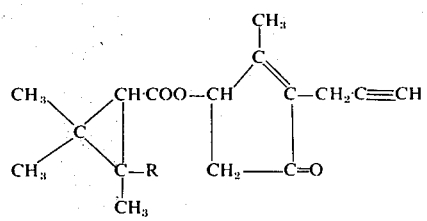

wherein R is hydrogen or methyl group, which is harmless to warm-blooded animals.

3 Claims, No Drawings

INSECTICIDAL COMPOSITION CONTAINING CYCLOPROPANE-CARBOXYLATE

This is a division of application Ser. No. 364,271, filed May 29, 1973, now U.S. Pat. No. 3,876,681.

This invention relates to novel cyclopropanecarboxylic acid esters, to a process for preparing the said esters, and to insecticidal composition containing the said esters.

More particularly, the present invention pertains to cyclopropanecarboxylic acid esters represented by the formula (I),

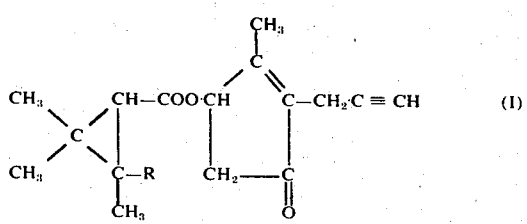

wherein R is hydrogen atom of methyl group.

Specific examples of the cyclopropanecarboxylate (I) are in Table 1.

Various insecticides of the cyclopropanecarboxylic acid ester type, such as pyrethrin or allethrin, have heretofore been known and widely been used for the control of sanitary injurious insects and agricultural and horticultural injurious insects because of their such excellent insecticidal properties that they are not only high in insecticidal activity but also low in toxicity to mammals and quick in knock-down effect on injurious insects.

Recently, it is the most important problem to control mosquitoes carrying encephalitis, filariasis or other infection diseases, among domestic injurious insects. As the most suitable insecticide such fumigants as mosquito coils, electric mosquito killer mats and the like containing pyrethrin or allethrin as an active ingredient are commercially used according to their easiness to use, low costs to prepare and the like.

The present inventors have made a large number of researches to synthesize various cyclopropanecarboxylic acid esters and examined biological activities thereof. As the result, present inventors have found that the present compounds of the formula (I) have far more excellent insecticidal activities when used in the form not only of oil sprays, emulsifiable concentrate and aerosols, but particularly, of fumigant.

Therefore an object of the present invention is to provide novel carboxylic acid esters excellent in insecticidal activity.

Another object is to provide a process for preparing novel carboxylic acid esters excellent in insecticidal activity.

Further object is to provide insecticidal compositions containing novel carboxylic acid esters as active ingredients.

The insecticidal effects of the ester compound obtained by reacting 2-propargyl-3-methyl-4-hydroxy-2-cyclopentene-1-on (alcohol moiety of the present ester) represented by the formula (II),

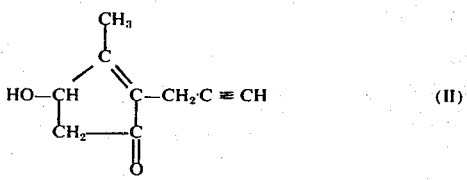

with chrysanthemic acid have been reported by Gersdorff and Piquett [(Gersdorff, Piquett; J. Econ. Entomol 54, 1250 (1961)].

According to the report, the effect of this chrysanthemic acid ester to house flies was only 64% of that of the composition containing allethrin in the turn table method of oil sprays. The present inventors attempted the modification of the homologs of this chrysanthemic acid esters and examined the insecticidal effects of the present esters. As the result, the present inventors have found that the present esters of the formula (I) have more excellent known down effect and killing effect than that of allethrin, and moreover vapor pressure of present compounds was higher than that of allethrin. Therefore, present inventors have found that the present compounds exhibit far more excellent insecticidal effects in particular when used as fumigant.

Table 1

| Compound No. | Name | Formula |
|---|---|---|
| 1 | 2-propargyl-3-methyl-2-cyclopentene-1-on-4-yl 2',2',3'-trimethyl-cyclopropanecarboxylate | (structure) |
| 2 | 2-propargyl-3-methyl-2-cyclopentene-1-on-4-yl 2',2',3',3'-tetramethyl-cyclopropanecarboxylate | (structure) |

2,2,3-Trimethylcyclopropanecarboxylic acid and 2,2,3,3-tetramethylcyclopropanecarboxylic acid (the acid moiety of the present ester) can be prepared by the method of Matsui and Kitahara [described in "Agr. Biol. Chem. 31, 1143 (1967)"], and these acids can be synthesized more easily and at lower costs. As the result, the present esters of the formula (I) can be also obtained at far lower costs and have more excellent practity than that of known insecticides of pyrethroid type.

The present esters of the formula (I) are novel compounds and can be obtained by reacting 2-propargyl-3-methyl-4-hydroxy-2-cyclopentene-1-on with cyclopropanecarboxylic acid or reactive derivative thereof represented by the formula (III),

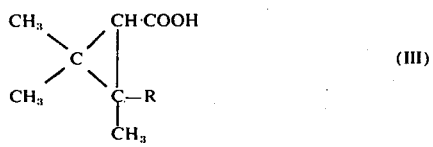

wherein R is the same meanings as defined above, if necessary, in the presence of auxiliary agent.

Embodiments of the above mentioned reactive derivative include acid halide and acid anhydride.

In accordance with the process of the present invention, in case a carboxylic acid of the formula (III) is used, the reaction is carried out under dehydration conditions. That is, the acid is reacted at room temperature or at an elevated temperature with cyclopentenone of the formula (II) in a suitable inert solvent in the presence of a dehydrating agent such as dicyclohexyl carbodiimide, whereby a desired ester can be obtained in a high yield.

In case an acid halide is used as a reactive derivative of the carboxylic acid of the general formula (III), the reaction can be sufficiently accomplished at room temperature by reacting the acid halide with a cyclopentenolone of the formula (II), using as a hydrogen halide-removing reagent such as organic tertiary base as pyridine, triethylamine or the like. The acid halide used in this case may be any of the halides within the scope of the present invention, but is ordinarily an acid chloride. In the reaction, the use of a solvent is desirable for smooth progress of the reaction, and such an inert solvent as benzene, toluene or petroleum benzine is ordinarily used. The acid halide of the formula (III) which is used in the present invention may be prepared easily according to the ordinary procedure comprising halogenating the carboxylic acid with thienyl halide, phosphorous polyhalide or the like.

In case an acid anhydride is used as a reactive derivative of the carboxylic acid of the formula (III), no auxiliary agent is particularly required, and the object can be accomplished by reacting the acid anhydride with a cyclopentenone of the formula (II). In this case, the elevation of temperature is preferable for acceleration of the reaction, and the use of an inert solvent such as toluene or xylene is preferable for smooth progress of the reaction, though not always indispensable.

The acid anhydrides which are used in the present invention may be prepared easily by refluxing the carboxylic acid of the formula (III) with, for example, an acetic acid anhydride under heating, and the carboxylic acid recovered in the esterification reaction can be used repeatedly with the acid anhydride.

Procedures for preparation of the present invention are illustrated with reference to the following examples.

EXAMPLE 1

A solution of 5.3 g of 2-propargyl-3-methyl-4-hydroxy-2-cyclopentene-1-on and 4.2 g of pyridine in 25 ml of dry benzene was cooled with ice, and a solution of 5.3 g of 2,2,3-trimethylcyclopropanecarbonyl chloride in 15 ml of dry benzene was added dropwise thereto. The resulting reaction mixture was sealed and left overnight. After the reaction mixture was poured into ice water, the organic layer was separated and washed with 5% (by weight) aqueous hydrochloric acid solution, 5% (by weight) aqueous sodium carbonate solution and an aqueous solution saturated with sodium chloride, and then dried over anhydrous magnesium sulfate. Benzene was evaporated to obtain 9.1 g of yellowish oil. Distillation under a reduced pressure gave 7.9 g of a yellowish oil of 2-propargyl-3-methyl-2-cyclopentene-1-on-4-yl-2',2',3'-trimethylcyclopropanecarboxylate ($n_C^{25}$: 1.4988).

| Elementary Analysis | C % | H % |
| --- | --- | --- |
| Found | 73.91 % | 7.74 % |
| Calculated | 73.82 % | 7.74 % |

EXAMPLE 2

A solution of 5.3 g of 2-propargyl-3-methyl-4-hydroxy-2-cyclopentene-1-on and 2,2,3-trimethylcyclopropanecarboxylic anhydride dissolved in 60 ml of toluene was refluxed for 4 hours. After cooling, the resulting reaction mixture was washed with 5% aqueous sodium carbonate and an aqueous solution saturated with sodium chloride. The organic layer was dried over anhydrous magnesium sulfate and distilled under reduced pressure. The crude oily product was purified with silica gel columnchlomatography to obtain 8.0 g of the same ester compound of Example 1.

EXAMPLE 3

To a solution of 5.3 g of 2-propargyl-3-methyl-4-hydroxy-2-cyclopentene-1-on and 4.5 g of 2,2,3-trimethylcyclopropanecarboxylic acid dissolved in 100 ml of methylenechloride, 7.9 g of dicyclohexycarbodiimide was added thereto. The resulting reaction mixture was stirred at room temperature for 24 hours and heated for 3 hours to complete the reaction. After cooling, the deposited dicyclohexylurea was separated and then the similar manner as in the operational procedure of the Example 1 is effected to obtain 7.6 g of the same ester compound of Example 1.

EXAMPLE 4

A solution of 5.3 g of 2-proparagyl-3-methyl-4-hydroxy-2-cyclopentene-1-on and 4.2 g of pyridine in 25 ml of dry benzene was cooled with ice, and a solution of 5.9 g of 2,2,3,3-tetramethylcyclopropanecarbonyl chloride in 15 ml of dry benzene. The resulting reaction mixture was sealed and left overnight. After the reaction mixture was poured into ice water, the organic layer was separated and washed with 5% (by weight) aqueous hydrochloric acid solution, 5% (by weight) aqueous sodium carbonate solution and an aqueous solution saturated with sodium chloride and then dried over anhydrous magnesium sulfate. Benzene was evaporated to obtain 9.6 g of yellowish oil. Distillation under a reduced pressure gave 8.5 g of a yellowish oil of 2-propargyl-3-methyl-2-cyclopentene-1-on-4-yl-2′,2′,3′,3′-tetramethylcyclopropanecarboxylate ($n_D^{25}$: 1.5011).

| Elementary Analysis | C % | H % |
|---|---|---|
| Found | 74.49 | 8.10 |
| Calculated | 74.42 | 8.08 |

EXAMPLE 5

To a solution of 5.3 g of 2-propargyl-3-methyl-4-hydroxy-2-cyclopentene-1-on and 5.9 g of 2,2,3,3-tetramethylcyclopropanecarboxylic acid in 100 ml of methylenechloride, 7.9 g of dicyclohexycarbodiimide was added thereto and the resulting mixture was left overnight. After the deposited dicyclohexyl urea was filtered, the similar operation procedure described in Example 4 gave 8.3 g of the same ester compound of Example 4.

In order to make it clear whether the present compounds are superior or not in insecticidal effect to not only the commercially available allethrin but the corresponding chrysanthemic acid ester, comparisons in effectiveness are shown below with reference to Experimental Examples.

EXPERIMENTAL EXAMPLES

Each 0.3% or 0.6% by weight of mosquito coils, containing as an active ingredient present compounds (1) or (2); corresponding chrysanthemic acid ester, technical allethrin, corresponding trimethyl cyclopropanecarboxylic acid ester or corresponding tetramethyl cyclopropanecarboxylic acid ester, were prepared according to the ordinary procedure.

Into a (70 cm)$^3$ glass chamber were liberated about 20 adults of Northern house mosquitoes. 1 g of each of the mosquito coils obtained above was ignited at both ends placed at the center of the bottom of the chamber. After ignition of the mosquito coil, the number of knocked down mosquitoes were counted with lapse of time for 24 minutes to calculate a knock down ratio at each time. At the same time, a 50% knock down time ($KT_{50}$) was calculated.

At every time after 24 minutes, knocked down mosquitoes were taken out, removed, fed and allowed to stand for oneday in the room for observation, and the numbers of alive and dead mosquitoes were observed to calculate the ratio of killed insects.

The results obtained were as set forth in Table I.

Table I

| No. | Test compound No. | Formula | 0.3 % mosquito coil $KT_{50}$ (min. sec) | Killing ratio (%) | 0.6 % mosquito coil $KT_{50}$ (min. sec) | Killing ratio (%) |
|---|---|---|---|---|---|---|
| 1 | Present compound (1) | [structure] | 4′42″ | 96 | 2′3″ | 100 |
| 2 | Present compound (2) | [structure] | 3′12″ | 100 | 2′00″ | 100 |
| 3 | Corresponding chrysanthemic acid ester of the present compound (1) | [structure] | 9′ | 72 | 6′06″ | 93 |
| 4 | Allethrin | [structure] | 10′48″ | 31 | 7′36″ | 77 |

As is clear from the above-mentioned Experimental Examples, the present compounds exhibit not only more quick knock down effect than that of allethrine widely used as fumigant, but also excellent killing effect. And the present compounds have more excellent effect than that of the corresponding chrysanthemic acid esters.

The present compounds of the formula (I) which is an active ingredient of the present invention, may not only be used singly but may be incorporated with suitable amounts of phenol or bisphenol derivatives such as BHT or the like, or arylamines such as phenyl-α-naphthylamine, phenyl-β-naphthylamine or condensation product of phenetidine with acetone, whereby compositions which have been more stabilized in insecticidal effects can be obtained. Further, the compositions may be increased in insecticidal activity by incorporation of synergists for pyrethroid type insecticides such as N-(2-ethyl-hexyl)-bicyclo[2,2,1]hepta-5-ene-2,3-dicarboxyimide (hereinafter referred to as "MGK-264"), octachlorodipropyl ether [hereinafter referred to as "S-421"], α-[2-(2-butoxyethoxy)ethoxy]-4,5-methylenedioxy-2-propyl toluene (hereinafter referred to as "piperonylbutoxide"), 4-(3,4-methylendioxyphenyl)-5-methyl-1,3-dioxane (hereinafter referred to as "Sufroxane"), and the known synergists.

Furthermore, the present compounds can display wider insecticidal activities when used in combination of 2 or more, and can be enhanced in insecticidal effect when used in admixture with other physiologically active materials, e.g. pyrethrin, allethrin, d-transallethrin, N-(chrysanthemoxymethyl)-3,4,5,6-tetrahydrophthalimide, dimethylmaleimidomethyl chrysanthemate, 5-benzyl-3-furylmethyl chrysanthemate, 5-propargylfurfuryl chrysanthemate, 5-propargyl-2-methyl-3-furylmethyl chrysanthemate, 3-phenoxybenzyl chrysanthemate, and optical isomers thereof or derivatives such as corresponding tetra- or tri-methylcyclopropane carboxylic acid esters of the above mentioned chrysanthemic acid esters, other insecticides or pyrethroid type, other insecticides such as BHC, Diazinone, phenitrothion, DDVP and the like.

In preparing the insecticidal compositions of the present invention, the present compounds may be formulated into oil sprays, emulsifiable concentrates, dusts, aerosols, wettable powders, granules, mosquito coils and other heating or non-heating fumigants according to the procedures thoroughly known to those skilled in the art, using diluting adjuvants for general insecticides like in the case of the conventional pyrethroides. Alternatively, they may be formulated into death-inducing powder or solid preparations incorporated with baits or other substances attractive for injurious insects.

Procedures for the preparation of the present compositions and biological effects thereof are illustrated below with reference to the blending examples and test examples, but it is needless to say that the scope of the present invention is not limited to the examples.

BLENDING EXAMPLE 1

Each 0.3 g of the present compounds (1) or (2) is dissolved in 5 ml of methanol and the each mixture is sufficiently mixed with 60 g of pyrethrum marc, 30 g of Tabu powder and 9.7 g of wood flour. The each mixture is sufficiently kneaded with 100 ml of water, and then shaped and dried to obtain 100 g of mosquito coil.

If necessary, the mosquito coil may be colored by addition of 5% of a dye such as Malachite Green or the like, or may be incorporated with a phenol or p-hydroxybenzoic acid ester.

BLENDING EXAMPLE 2

To 0.25 g of the present compound 0.1 g of each allethrin, d-trans allethrin, dimethylmaleimidomethyl chrysanthemate, dimethylmaleimidomethyl-2,2,3,3-tetramethylcycopropanecarboxylate or 5-propargylfulfuryl chrysanthemate is added, and the each mixture is dissolved in 5 ml of methanol.

These mixtures are operated by the same manner as described in the Blending Example 1 to obtain each combined mosquito coil.

BLENDING EXAMPLE 3

Each 0.2 g of the present compound (1) or (2) and each 0.5 g of S-421 are dissolved in chloroform. This each solution is uniformly absorbed on the surface of an asbestos piece of 2.5 cm × 1.5 cm in area and 0.3 cm in thickness. Onto the asbestos surface is pasted another asbestos piece identical in size therewith to obtain respective insecticidal fibrous fumigant compositions for use on an electrically heated plate. As the fibrous carrier, there may be used, in addition to asbestos, a pulp sheet or the like material which is identical in effectiveness therewith.

BLENDING EXAMPLE 4

A mixture comprising 0.2 g of the present compound (2) and 0.05 g of DDVP is dissolved in chloroform. This solution is treated in the same manner as in Blending Example 3 to obtain the respective insecticidal fibrous fumigant composition for use on an electrically heated plate.

BLENDING EXAMPLE 5

To 0.2 g of the present compound (2) 0.1 g of each 5-benzyl-3-furylmethyl chrysanthemate, 5-benzyl-3-furylmethyl-2',2',3'-trimethylcyclopropanecarboxylate or 3-phenoxybenzyl-2',2',3',3'-tetramethylcyclopropanecarboxylate is added, and in addition to these mixture each 0.6 g of BHT is added thereto and the each resulting mixture is dissolved in 5 ml of methanol. 60 G of pyrethrum marc, 30 g of Tabu powder and 9.1 g of wood flour are added to each mixture and mixed sufficiently. These mixture are operated by the same manner as described in the Blending Example 1 to obtain each combined mosquito coil.

BLENDING EXAMPLE 6

A mixture comprising 0.1 part by weight of the present compound (2) and 0.5 part by weight of piperonyl butoxide was dissolved in deodorized kerosene to make the total amount 100 parts, whereby oil spray obtained.

BLENDING EXAMPLE 7

A mixture comprising 20 parts by weight of the present compound (2), 10 parts by weight of Sorpol SM-200 (registered trade mark of Toho Chemical Co.) and 70 parts by weight of xylene was thoroughly stirred to obtain emulsifiable concentrate.

BLENDING EXAMPLE 8

A mixture comprising 0.4 part by weight of the present compound (1), 2 parts by weight of p,p'- dichlorodiphenyl trichloroethane, 6 parts by weight of xylene and 6.6 parts by weight of deodorized kerosene was mixed and packed in the aerosol container.

After attaching a valve portion to the container, 85 parts by weight of a propellant (i.e. freon, vinyl chloride monomer, liquefied petroleum gas and the like) was introduced under pressure through said valve portion into the container to obtain an aerosol.

BLENDING EXAMPLE 9

0.3 Part by weight of the present compound (1) was dissolved in deodorized kerosene to make the total amount 100 parts, whereby oil spray was obtained.

BLENDING EXAMPLE 10

A mixture comprising 0.4 part by weight of the present compound (2), 0.3 part by weight of 0,0-dimethyl-0-(3-methyl-4-nitrophenyl)thiophosphate, 6 parts by weight of xylene and 8.3 parts by weight of deodorized kerosene was mixed and treated in the same manner as in Blending Example 8 to obtain an aerosol.

BLENDING EXAMPLE 11

A mixture comprising 5 parts by weight of the present compound (2), 5 parts by weight of toyolignin CT (registered trade mark of Toyo Spinning Co.) and 90 parts by weight of GSM clay (registered trade mark of Zieglite Mining Co.) was thoroughly stirred in a mortar. Subsequently, the mixture was kneaded 10% by weight, based on the amount of said mixture, of water and granulated by means of a granulator, followed by air-drying, to obtain granule.

BLENDING EXAMPLE 12

A mixture comprising 25 parts by weight of the present compound (1), 1.5 parts by weight of Sorpol 5029-0 (registered trade mark of Toho Chemical Co.) and 3.5 parts by weight of lignin was mixed and 70 parts by weight of diatomaceous earth were added thereto. The resulting mixture was thoroughly stirred in a mortar to obtain wettable powder.

BLENDING EXAMPLE 13

To a solution of 1 part by weight of the present compound (2) in 20 parts by weight of acetone was added 99 parts by weight of 300 mesh diatomaceous earth. The resulting mixture was thorougly stirred in a mortar, and then the acetone was vaporized to obtain dust.

Insecticidal effects of the thus obtained compositions of the present invention are as set forth in the examples shown below.

EXAMPLE 6

Into a (70 cm)$^3$ grass chamber were liberated about 50 adults of Northern house mosquitoes 0.2 Grams of each of the mosquito coils obtained according to Examples 1, 2 and 5 was ignited at both ends placed at the center of the bottom of the chamber. The smoke inside the chamber was stirred by means of a small motor fan (blade diameter 13 cm). As the result, every mosquito coil could knock down more than 90% of the mosquito adults within 20 minutes and could kill more than 80% of the insects on the next day.

EXAMPLE 7

Into a (70 cm)$^3$ glass chamber were liberated about 50 adults of house flies. 0.2 Grams of each of the mosquito coils obtained according to Examples 2 and 5 was ignited at both ends placed at the center of the bottom of the chamber. The smoke inside the chamber was stirred by means of a small motor fan (blade diameter 13 cm). As the result, every mosquito coil could knock down more than 80% of the mosquito adults within 20 minutes and could kill more than 60% of the insects on the next day.

EXAMPLE 8

Into a (70 cm)$^3$ glass chamber were liberated about 50 adults of Northern house mosquitoes. Each of the insecticidal fibrous fumigant compositions obtained according to Examples 3 and 4 was put on an electric heating means, which was then placed at the center of the bottom of the chamber. Subsequently, an electric current was applied to the heating means, and the interior of the chamber was stirred by means of a small motor fan (blade diameter 13 cm). As the result, every composition could kill more than 90% of the mosquito adults within 20 minutes, and could kill more than 80% of the insects on the next day.

EXAMPLE 9

According to the campbell's turn table method [disclosed in "Soap & Sanitary Chemicals", Vol. 14, No. 6, page 119 (1938)], 5 ml of the each oil sprays obtained in Blending Example 9 was sprayed using 0.3% oil spray, 0.15% oil spray diluted with deodorized kerosene and 0.075% oil diluted with deodorized kerosene. Adults of house flies (a group of about 100 flies) were exposed to the settling mist for 10 minutes. Thereafter, the flies were taken out, fed and allowed to stand in a constant temperature room at 27°C, and the numbers of alive and dead were observed after 24 hours to calculate the ratio of killed insects.

Insecticidal effect of oil spray obtained in the above Blending Example 9 to the house fly adults was measured by the $LC_{50}$ (50% lethal concentration). The results obtained were as set forth in Table 2.

Table 2

| | Insecticidal composition (oil spray) | $LC_{50}$ (%) |
|---|---|---|
| 1 | Present compound (1) | 0.047 |
| 2 | Allethrin | 0.095 |
| 3 | Pyrethrin | 0.052 |

EXAMPLE 10

About 20 adults of house flies were liberated in a (70 cm)$^3$ glass chamber, and 0.7 ml of each of the oil sprays obtained in Blending Example 9 was sprayed into the chamber under a pressure of 20 pounds/in$^2$ by use of a glass-made atomizer.

Thereafter, the numbers of knocked down house flies was counted to calculate the $KT_{50}$ (50% knock down time) of each compound. The results obtained were as set forth in Table 3.

Table 3

| | Insecticidal composition (oil spray) | $KT_{50}$ (second) |
|---|---|---|
| 1 | Present compound (1) | 105 |
| 2 | Allethrin (0.2 %) | 130 |
| 3 | Pyrethrin (0.2 %) | 120 |

EXAMPLE 11

About 20 adults of Northern house mosquitoes were liberated in a $(70 \text{ cm})^3$ glass chamber, and 0.7 ml of each of the diluted oil sprays, obtained in Blending Example 9, with deodorized kerosene to contain 0.1% by weight of active ingredient was sprayed into the chamber under a pressure of 20 pounds/in$^2$ by use of a glass-made atomizer. Thereafter, the numbers of knocked down Northern house mosquitoes were counted to calculate the $KT_{50}$ (50% knock down time). The results obtained were set forth in Table 4.

Table 4

| | Insecticidal composition (oil spray) | $KT_{50}$ (second) |
|---|---|---|
| 1 | Present compound (1) | 70 |
| 2 | Allethrin (0.1 %) | 125 |
| 3 | Pyrethrin (0.1 %) | 105 |

EXAMPLE 12

According to the Campbell's turn table method [described in Example 9], 5 ml of each of the oil sprays obtained in Blending Example 6 was sprayed, and adults of house flies (a group of about 100 flies) were exposed to the settling mist for 10 minutes. Thereafter, the flies were taken out, fed and allowed to stand in a constant room temperature at 27°C, and the numbers of alive and dead were observed after 24 hours to calculate the ratio of killed insects. The results obtained were set forth in Table 5.

Table 5

| Insecticidal composition | Knock down ratio (%) After 10 min. | After 1 day |
|---|---|---|
| Present compound (2) | 100 | 100 |

EXAMPLE 13

About 20 adults of house flies were liberated in a $(70 \text{ cm})^3$ glass chamber, the aerosol obtained in Blending Example 8 or 10 was sprayed 1 second, and the knocked down flies were observed after 15 minutes. The only knocked down flies were collected, removed to the new observation cage, fed and the numbers of alive and dead were observed after 1 day. The results obtained were set forth in Table 6.

Table 6

| Insecticidal composition | Knock down ratio (%) After 15 minutes | Ratio of killed insects (%) After 1 day |
|---|---|---|
| 1 Aerosol of Blending Example 8 | 100 | 86 |
| 2 Aerosol of Blending Example 10 | 100 | 72 |

EXAMPLE 14

Into a 300 milliliter-glass beaker containing 200 ml of each solution of emulsifiable concentrate obtained in Blending Example 7 and of wettable powder obtained in Blending Example 12, prepared to the tested concentration with water, about 30 full-grown larvae of Northern house mosquitoes were liberated in the case. The numbers of alive and dead were observed after 1 day to calculate the $LC_{50}$ (50% lethal concentration). The results obtained were as set forth in Table 7.

Table 7

| Insecticidal composition | $LC_{50}$ (p.p.m.) |
|---|---|
| Emulsifiable concentrate of Blending Example 7 | 0.02 |
| Wettable powder of Blending Example 12 | 0.09 |
| Wettable powder of Allethrin | 0.10 |

EXAMPLE 15

Into a 14 liter-polyethylene backet coontaining 10 liters of water was charged 400 mg. of granule obtained in Blending Example 11. After 1 day, full-grown larvae of Northern house mosquitoes were liberated in the water, and then the alive and dead of the larvae were observed. As the result, more than 90% of the larvae could be killed within 24 hours.

EXAMPLE 16

Onto the bottom of a grass Petri dish of 14 cm. in diameter and 7 cm in height was uniformly dusted by 2 g/in$^2$ of the dust obtained in Blending Example 13, and the dish was coated on the inner wall with butter, leaving at the lower part an uncoated portion of about 1 cm in width. Subsequently, a group of 10 German cockroach adults were liberated in the dish and contacted with the dust for 30 minutes. As the result, 100% of the cockroaches were knocked down, and 100% of the knocked down cockroaches could be killed on the third day after the contact.

What is claimed is:

1. An insecticidal composition comprising an inert carrier and an insecticidally effective amount of a compound of formula

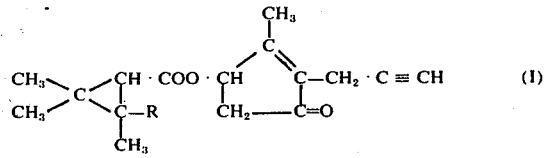

wherein R is hydrogen or methyl group.

2. A composition according to claim 1, wherein the composition is in the form of oil spray, emulsifiable concentrate, dust, aerosol, wettable powder, granule, mosquito coil, heating fumigant, non-heating fumigant or bait.

3. A process for controlling insects by contacting the insects with an insecticidally effective amount of the compound of claim 1.

* * * * *